(12) United States Patent
Arpino (10) Patent No.: US 10,184,889 B2
(45) Date of Patent: Jan. 22, 2019

(54) SENSOR DEVICE FOR OPTICALLY DETECTING CHARACTERISTICS OF A FLUID

(71) Applicant: BITRON S.P.A., Turin (IT)

(72) Inventor: Fabio Arpino, Milan (IT)

(73) Assignee: BITRON S.P.A., Turin (IT)

( * ) Notice: Subject to any disclaimer, the term of this patent is extended or adjusted under 35 U.S.C. 154(b) by 0 days.

(21) Appl. No.: 15/738,320

(22) PCT Filed: Jun. 29, 2016

(86) PCT No.: PCT/IB2016/053883
§ 371 (c)(1),
(2) Date: Dec. 20, 2017

(87) PCT Pub. No.: WO2017/002032
PCT Pub. Date: Jan. 5, 2017

(65) Prior Publication Data
US 2018/0202931 A1   Jul. 19, 2018

(30) Foreign Application Priority Data

Jun. 29, 2015   (IT) .................. 102015000028522

(51) Int. Cl.
*G01N 21/59* (2006.01)
*G01N 21/85* (2006.01)
(Continued)

(52) U.S. Cl.
CPC .......... *G01N 21/59* (2013.01); *A47L 15/4297* (2013.01); *D06F 39/004* (2013.01); *G01N 21/85* (2013.01)

(58) Field of Classification Search
CPC . A47L 15/4297; D06F 39/004; G01N 21/534; G01N 2201/062; G01N 2201/0218; G01N 21/59; G01N 21/85
See application file for complete search history.

(56) References Cited

U.S. PATENT DOCUMENTS

| | | | | |
|---|---|---|---|---|
| 4,257,708 A | * | 3/1981 | Fukuda | G01N 21/534 250/565 |
| 5,680,111 A | * | 10/1997 | Danby | A61M 5/365 250/573 |

(Continued)

FOREIGN PATENT DOCUMENTS

| DE | 197 14 695 A1 | 10/1998 |
|---|---|---|
| DE | 10 2011 102 627 A1 | 1/2012 |

(Continued)

OTHER PUBLICATIONS

Written Opinion of the International Searching Authority of PCT/IB2016/053883 dated Sep. 29, 2016.

(Continued)

*Primary Examiner* — Sang H Nguyen
(74) *Attorney, Agent, or Firm* — Sughrue Mion, PLLC (57) ABSTRACT

A sensor device for optically detecting characteristics of a fluid. The device includes a housing with a base portion from which first and second appendages extend at least partially facing one another, and between which in use a fluid is present, and first and second optoelectronic devices adapted to transmit and receive radiation, respectively, mounted at the first and second appendages of the housing, respectively. The arrangement is such that in use a radiation beam transmitted by the first optoelectronic device propagates in an optical path which includes a portion crossing the fluid between said appendages and reaches the second optoelectronic device. This optical path includes at least one reflecting surface made integrally in an appendage of the housing and adapted to deflect the radiation beam between the associated optoelectronic device and the fluid crossing portion.

14 Claims, 7 Drawing Sheets

(51) Int. Cl.
*A47L 15/42* (2006.01)
*D06F 39/00* (2006.01)

(56) References Cited

U.S. PATENT DOCUMENTS

| | | | | |
|---|---|---|---|---|
| 6,771,373 | B2* | 8/2004 | Schenkl | A47L 15/4297 |
| | | | | 356/442 |
| 7,230,687 | B2* | 6/2007 | O'Mahony | A61M 1/1692 |
| | | | | 210/96.2 |
| 8,169,622 | B1* | 5/2012 | Reith | G01N 21/534 |
| | | | | 200/511 |
| 8,531,670 | B2* | 9/2013 | Schenkl | G01N 21/534 |
| | | | | 250/574 |
| 8,834,646 | B2* | 9/2014 | Bewley, Jr. | A47L 15/4297 |
| | | | | 134/56 D |
| 8,920,356 | B2* | 12/2014 | Shang | A61M 1/16 |
| | | | | 210/645 |
| 2009/0140754 | A1* | 6/2009 | Schenkl | A47L 15/4297 |
| | | | | 324/693 |
| 2009/0310123 | A1* | 12/2009 | Thomson | G01N 33/49 |
| | | | | 356/40 |
| 2012/0001099 | A1* | 1/2012 | Schenkl | A47L 15/4297 |
| | | | | 250/574 |
| 2012/0090654 | A1* | 4/2012 | Bewley, Jr. | A47L 15/4297 |
| | | | | 134/56 D |

FOREIGN PATENT DOCUMENTS

| | | |
|---|---|---|
| EP | 0 792 486 B1 | 4/2000 |
| WO | 96/15495 A1 | 5/1996 |

OTHER PUBLICATIONS

International Search Report of PCT/IB2016/053883 dated Sep. 29, 2016.

* cited by examiner

SENSOR DEVICE FOR OPTICALLY DETECTING CHARACTERISTICS OF A FLUID

CROSS REFERENCE TO RELATED APPLICATIONS

This application is a National Stage of International Application No. PCT/IB2016/053883 filed Jun. 29, 2016, claiming priority based on Italian Patent Application No. 102015000028522 filed Jun. 29, 2015, the contents of all of which are incorporated herein by reference in their entirety.

BACKGROUND OF THE INVENTION

Field of the Invention

The present invention relates to a sensor device for optically detecting the characteristics of a fluid, such as the turbidity of the washing bath in a dishwasher or a washing machine.

More specifically, the invention relates to a sensor device of the type comprising:
- a housing having a base portion from which first and second appendages extend at least partially facing one another, and between which in use said fluid is present,
- first and second optoelectronic devices capable of transmitting and receiving radiation, respectively, mounted in the housing, in the first and second appendages, which are at least partially made of a material transparent to said radiation,
- the arrangement being such that in use a radiation beam transmitted by the first optoelectronic device propagates in an optical path which includes a portion crossing the fluid between said appendages and reaches the second optoelectronic device,
- wherein said optical path comprises at least one reflecting surface adapted to deflect the radiation beam between the associated optoelectronic device and said fluid crossing portion.

Background

Sensor devices of this type are described in DE 10 2011 102627 A1 and U.S. Pat. No. 8,169,622 B1. In the devices according to said prior documents, the reflecting surfaces which deflect the radiation beam are formed at the ends of one or two transparent bodies, made separately and distinctly from the housing of the device and mounted in the finger-like appendages of the housing. In these prior art devices, the optical path of the radiation beam extends in a plane essentially parallel to the longitudinal directions of said appendages of the housing of the device. The production of the devices according to the prior art is relatively complicated and costly.

One object of the present invention is to provide an improved type of sensor device.

SUMMARY OF THE INVENTION

This and other objects are achieved according to the invention with a sensor device of the type specified above, characterized in that said at least one reflecting surface is made integrally in one of said appendages of the housing.

Conveniently, said optical path extends in a plane at an angle, and preferably orthogonal, to the longitudinal directions of said appendages of the housing.

In one embodiment, the aforesaid optical path comprises first and second reflecting surfaces made in the first and second appendages of the housing, respectively,
- the first reflecting surface being adapted to deflect the radiation beam transmitted by the first optoelectronic device towards the aforesaid fluid crossing portion,
- the second reflecting surface being adapted to deflect the beam from said crossing portion towards the second optoelectronic device.

Conveniently, the first and second optoelectronic devices may be mounted on two portions of the same circuit board, which each extend in one of said appendages of the housing, said optoelectronic devices being orientated so that the beam transmitted by the first and the beam received by the second are essentially parallel to one another.

BRIEF DESCRIPTION OF THE DRAWINGS

Further embodiments, characteristics and advantages of the invention will be apparent from the following detailed description, provided purely by way of non-limiting example, with reference to the appended drawings, in which.

DETAILED DESCRIPTION OF THE INVENTION

Figure 1:
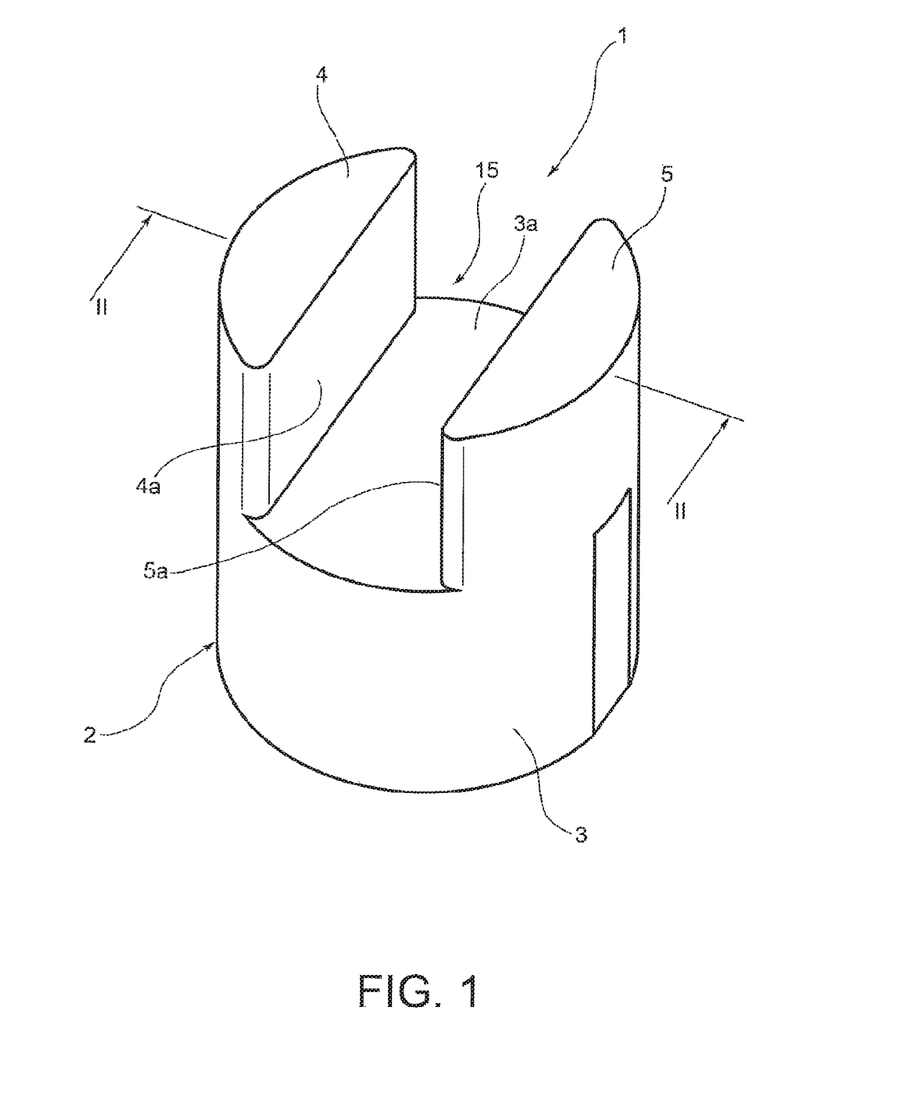
FIG. 1 is a perspective view of a sensor device for optically detecting characteristics of a fluid according to the present invention.
Figure 2:
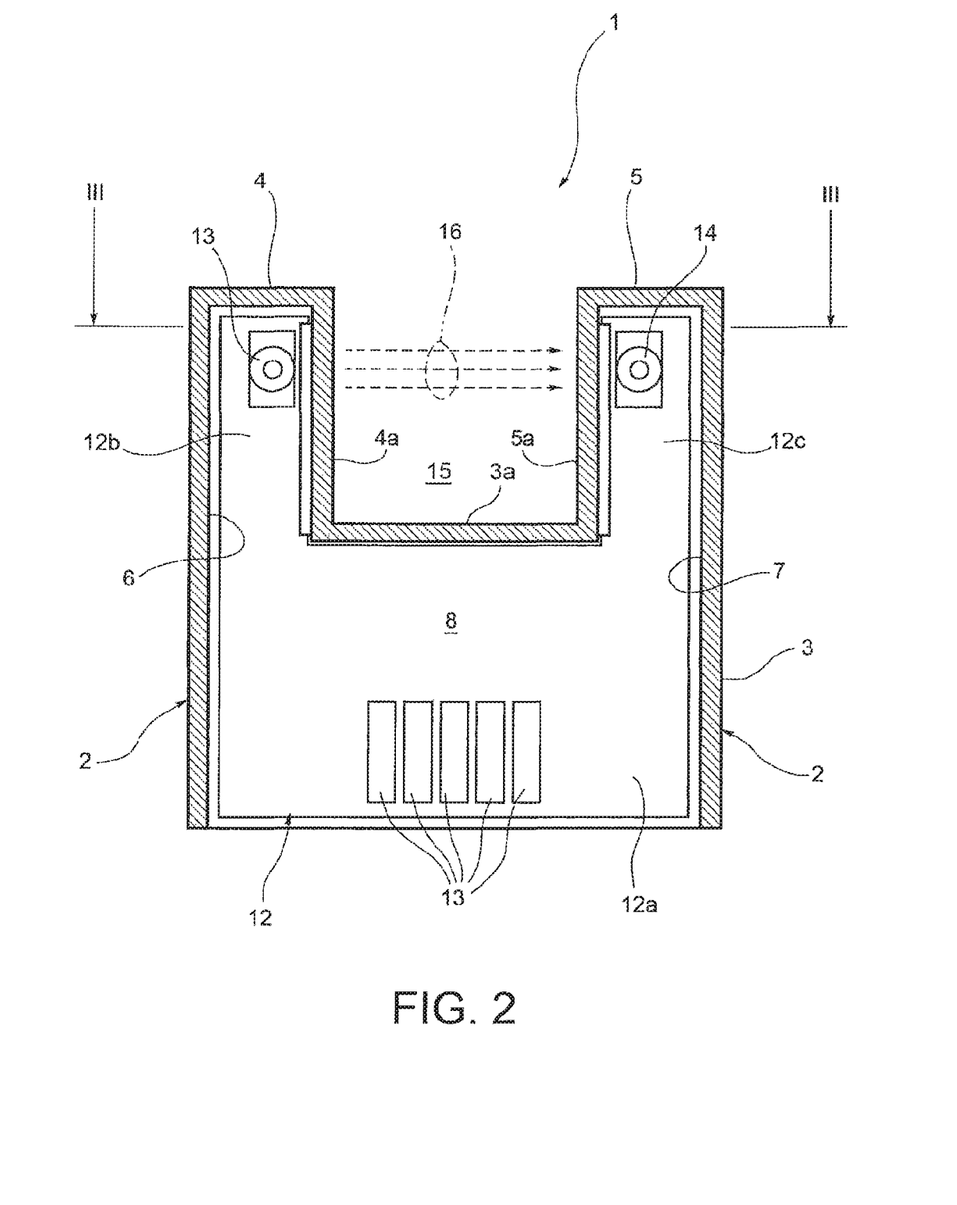
FIG. 2 is a partial sectional view taken along the line of FIG. 1.

In the drawings, and particularly in FIG. 1, the number 1 denotes the whole of a sensor for optically detecting characteristics of a fluid, made according to the present invention.

The sensor device 1 comprises a housing 2, including a base portion 3 from which first and second finger-like hollow appendages 4, 5 extend in the same direction, at least partially facing one another.

In use, the fluid of which at least one characteristic, such as the degree of turbidity, is to be optically detected is present in the region outside the housing 2 and between the appendages 4 and 5.

In the embodiment illustrated by way of example, the base portion 3 of the housing 2 has an essentially flat top surface 3a, and the appendages 4 and 5 each have a half-moon profile in cross section. The facing surfaces 4a and 5a of the appendages 4 and 5 are essentially flat and parallel to one another.

At least the appendages 4 and 5, but preferably the whole housing, are made of a moulded plastic material which is transparent to the radiation used.

With reference to FIGS. 2 to 5, in the appendages 4 and 5 of the housing 2 there are formed respective cavities 6 and 7, communicating below with the cavity 8 formed inside the base portion 3 of said housing.

The housing 2 as a whole may be made from one piece of plastic material, preferably by injection moulding.

Figure 3:
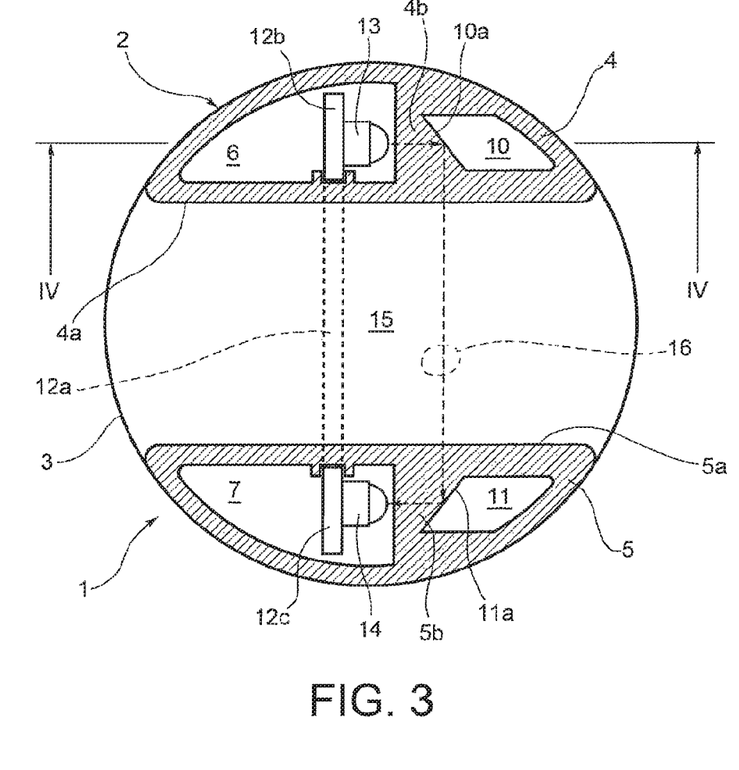
FIG. 3 is a partial sectional view taken along the line of FIG. 2.
Figure 4:
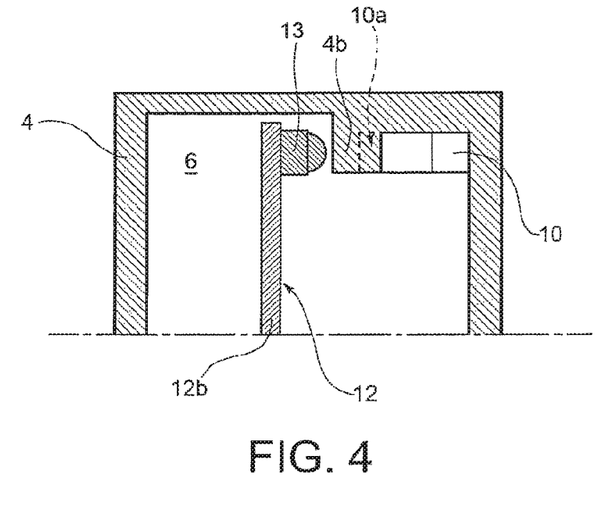
FIG. 4 is a partial sectional view taken along the line IV-IV of FIG. 3.
Figure 5:
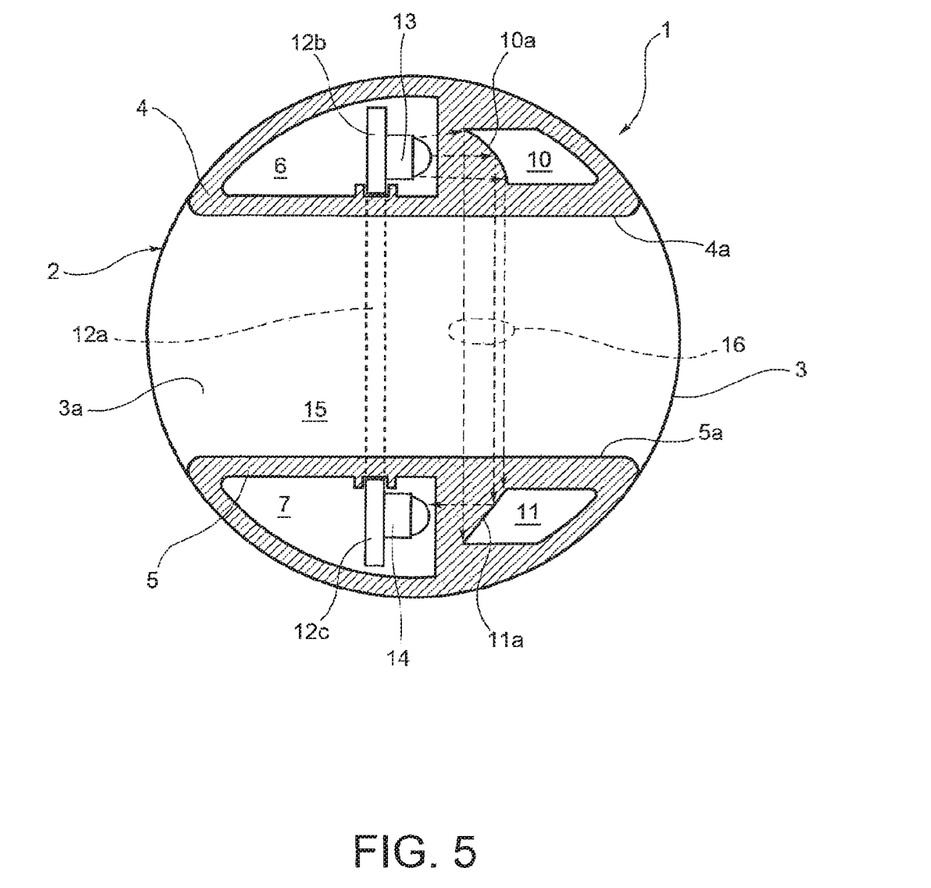
FIG. 5 is a sectional view similar to that given in FIG. 3, and shows a variant embodiment.

With reference to FIGS. 3 to 5, in the distal portion of each appendage 4, 5 there is formed a respective internal cavity 10, 11, opening below towards the base portion 3 of the housing 2.

The cavities 10 and 11 are made without undercuts, so that they can easily be formed during the injection moulding of the housing 2.

The functions of the cavities 10 and 11 are described below.

As can be seen in FIGS. 2 to 5, a circuit board 12 is positioned inside the housing 2, and comprises a base portion 12*a*, which extends into the cavity 8 and carries a plurality of conductive tracks 13 acting as connecting members for connection to external circuits (not shown).

The board 12 also has two appendages 12*b* and 12*c*, which protrude from the base portion 12*a* and extend into the cavities 6 and 7 inside the appendages 4 and 5 of the housing 2.

As can be seen in FIGS. 3 and 4, the appendages 12*b* and 12*c* of the circuit board 12 extend into the cavities 6 and 7 of the appendages 4 and 5 of the housing 2, at least to the height of their internal cavities 10 and 11.

An optoelectronic device 13 for transmitting radiation is mounted on the surface of the appendage 12*b* of the board 12 facing the cavity 10.

An optoelectronic device 14 for receiving radiation is mounted on the surface of the appendage 12*c* of the board 12 facing the cavity 11.

The device 13 is, for example, an emitting diode such as an LED.

The device 14 is, for example, a phototransistor.

In the embodiment shown in FIGS. 3 and 4, the optoelectronic devices 13 and 14 are orientated so that the beam transmitted by the first and the beam received by the second are essentially parallel to one another (although this arrangement is preferable, it is not essential). Additionally, the walls 10*a* and 11*a* of the cavities 10 and 11 which are nearest to the corresponding optoelectronic devices 13 and 14 (FIG. 3) are essentially flat, the wall 10*a* being inclined essentially at 45° to the direction of the beam transmitted by the optoelectronic device 13 and essentially at 90° to the surface 11*a*, which is orientated essentially at 45° to the axis of the beam of the optoelectronic device 14.

The arrangement is such that, in use, the optoelectronic device 13 transmits a radiation beam towards the surface 10*a* of the cavity 10, through a wall 4*b* of the appendage 4 of the housing 2.

The transparent plastic material of which the housing 2, or at least the housing appendages 4 and 5, are made has a refractive index such that the beam incident on the border surface 10*a* between the wall 4*b* and the internal cavity 10 undergoes total reflection and is deflected towards the other appendage 5 of the housing 2, as shown schematically in FIG. 3.

The surface 10*a* therefore acts as a reflecting surface, without having to be provided with any layer of reflective material. The reflection essentially takes place as a result of the difference between the refractive indices of the material forming the appendage 4, and particularly its wall 4*b*, and the air filling the internal cavity 10 of this appendage.

Downstream of the reflecting surface 10*a*, the radiation beam is propagated towards the appendage 5, passing through the channel-like region 15 delimited by the top surface 3*a* of the base portion 3 of the housing 2 and the facing surfaces or faces 4*a* and 5*a* of the appendages 4 and 5.

The optical path of the beam therefore comprises an intermediate portion, indicated by 16 in FIGS. 3 and 5, which in use extends through the fluid of which a characteristic is to be optically detected.

The radiation beam therefore passes through part of the appendage 5, until it reaches the border surface 11*a* between the wall 5*b* of this appendage and the corresponding internal cavity 11.

The surface 11*a* also acts as a surface for reflecting the radiation beam incident on it, as a result of the difference between the refractive indices of the material forming the appendage 5 and the air filling the internal cavity 11.

The reflecting surface 11*a* deflects the incident beam towards the receiving optoelectronic device 14.

The reflecting surfaces 10*a* and 11*a* can easily be formed integrally with the body of the housing 2, and enable the radiation beam to be reflected without the use of additional components.

These reflecting surfaces and the associated cavities 10 and 11 are conveniently made during the moulding of the housing 2, without the need for additional machining and/or processes, and therefore at practically no cost.

The production of the reflecting surfaces 10*a*, 11*a* by injection moulding provides the appropriate constancy in their positioning and the related optical performance.

Because of the distinctive orientation of the optoelectronic devices and the associated reflecting surfaces, the present invention enables the width of the light beam that can reach the photoreceiver to be limited to the beam reflected from said reflecting surfaces. The portion of the radiation beam transmitted by the first optoelectronic device, which is not deflected in the measurement area towards the second optoelectronic device, is orientated in directions which minimize its effect on the reading.

In the embodiment described above with reference to FIGS. 3 and 4, the reflecting surfaces 10*a* and 11*a* are essentially flat.

In the embodiment shown in FIG. 5, however, the reflecting surface 10*a* has a curved profile for the "concentration" or collimation of the beam reflected towards the other reflecting surface 11*a*.

If necessary, the reflecting surface 11*a* may also be of a non-planar type and may be shaped so as to concentrate the beam reflected towards the optoelectronic device 14.

Figure 6:
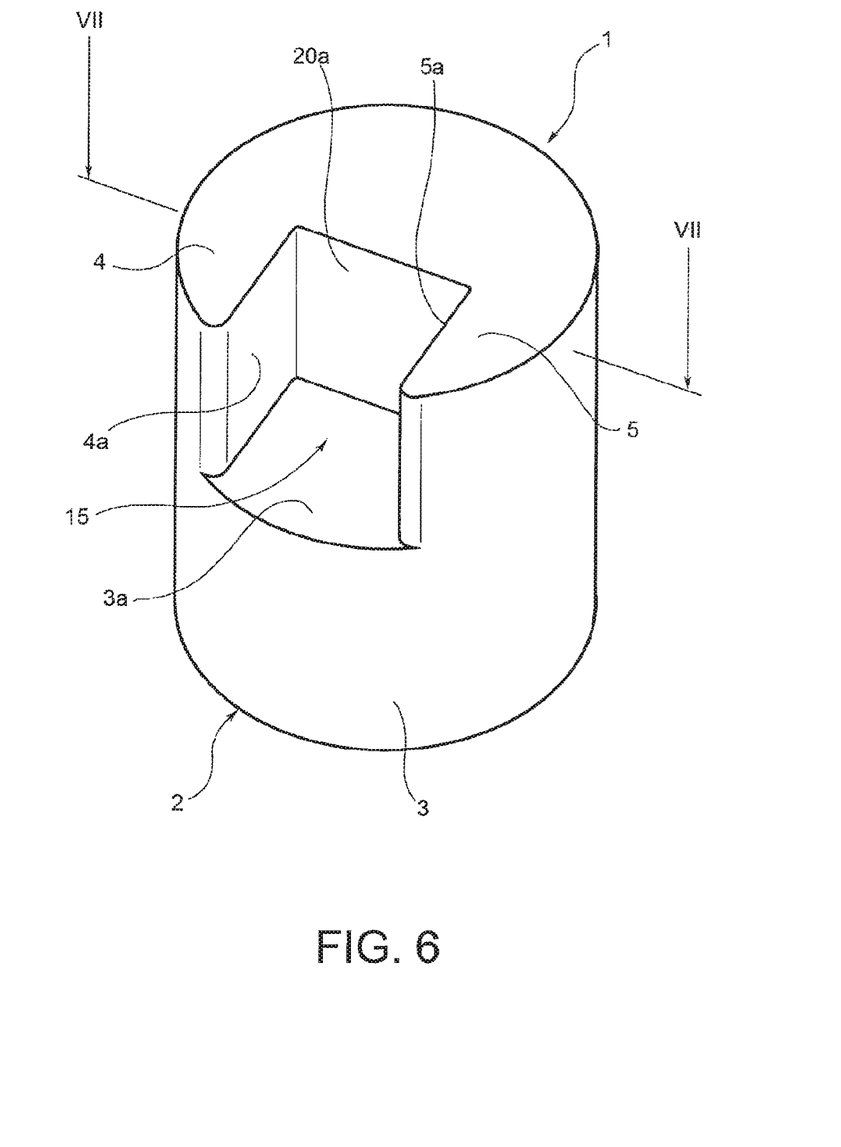
FIG. 6 is a perspective view of a variant embodiment.
Figure 7:
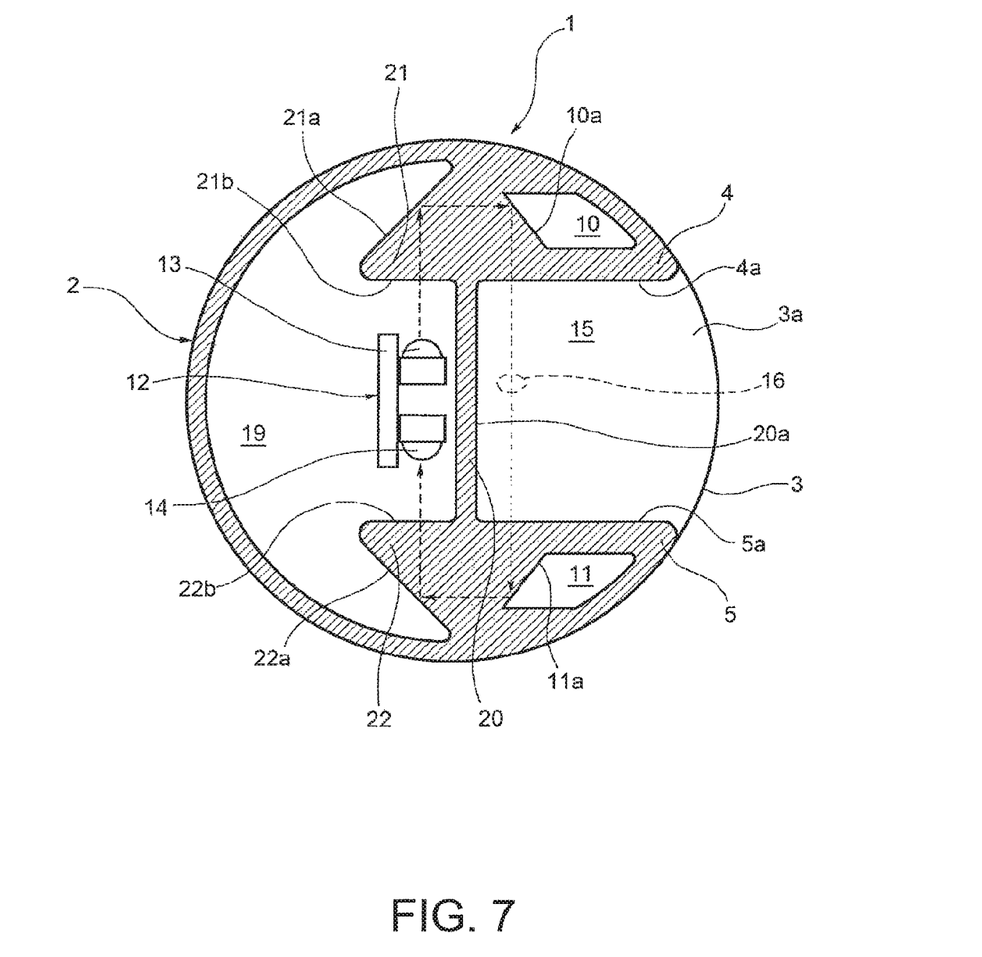
FIG. 7 is a partial sectional view taken along the line VII-VII of FIG. 6.

FIGS. 6 and 7 show a variant embodiment.

In these figures, parts and elements identical or essentially corresponding to parts and elements described previously have again been given the same reference numerals as those used previously.

With reference to FIG. 6, in this variant the housing 2 is essentially of generally cylindrical shape, and the region 15 lying between the appendages 4 and 5 is formed by a recess extending towards the inside of this housing 2 from its cylindrical side surface, and from part of its top surface. This recess or region 15 is delimited below by the horizontal surface 3*a*, and laterally by the facing surfaces or faces 4*a*, 5*a* of the appendages 4 and 5, as well as by a surface 20*a* which is essentially vertical and orthogonal to the surfaces or faces 3*a*, 4*a* and 5*a*.

As can be seen in FIG. 7, the surface 20*a* is the outer surface of a wall 20, which is made integrally with the housing 2 and which interconnects the appendages 4 and 5.

The wall 20 helps to delimit, together with the cylindrical wall portion of the top portion of the housing 2, an internal region 19, which communicates below with the inside of the base portion 3.

The transmitting optoelectronic device 13 and the receiving optoelectronic device 14 are carried by the same circuit board 12 as that which extends at the wall 20, and face in opposite directions towards internal formations 21 and 22 made in one piece with the housing 2.

The formation 21 has a surface 21b, planar for example, extending in a plane essentially orthogonal to the direction of the radiation beam transmitted by the transmitting device 13. This formation 21 also has a further vertical surface or face 21a, orientated essentially at 45° to the surface 21b and intended to act, in use, as a total reflection surface adapted to deflect the beam received from the transmitting device 13 towards the reflecting surface 10a formed in the cavity 10.

Similarly, the formation 22 has a surface 22a acting, in use, as a total reflection surface for the beam which is received from the optical path 16 and which is reflected towards this surface by the surface 11a of the cavity 11. The formation 22 has a further border surface 22b, orientated essentially at 45° to the surface 22a, and facing the receiving device 14.

The arrangement is such that the radiation beam transmitted, in use, by the optoelectronic device 13 passes through the formation 21, is reflected at the surfaces 21a and 10a, then passes through the region 15 lying between the appendages 4 and 5, and then penetrates into the appendage 5 and is reflected first by the surface 11a and subsequently by the surface 22a towards the receiving optoelectronic device 14.

Although all the reflecting surfaces 10a, 11a, 21a and 22a are shown as flat surfaces in FIG. 7, one or more of them may conveniently be shaped so as to impart a corresponding shape to the radiation beam which, in use, travels between the transmitting device 13 and the receiving device 14.

The variant shown in FIGS. 6 and 7 enables the size of the circuit board 12 to be reduced. Correspondingly, the overall size of the housing 2 can also be conveniently reduced.

With reference to FIG. 6, it can be seen that the shape of the housing shown therein may also be used in a device in which the optoelectronic elements 13 and 14 and the associated reflecting surfaces 10a and 11a are arranged as shown in FIGS. 1 to 5.

Figure 8:
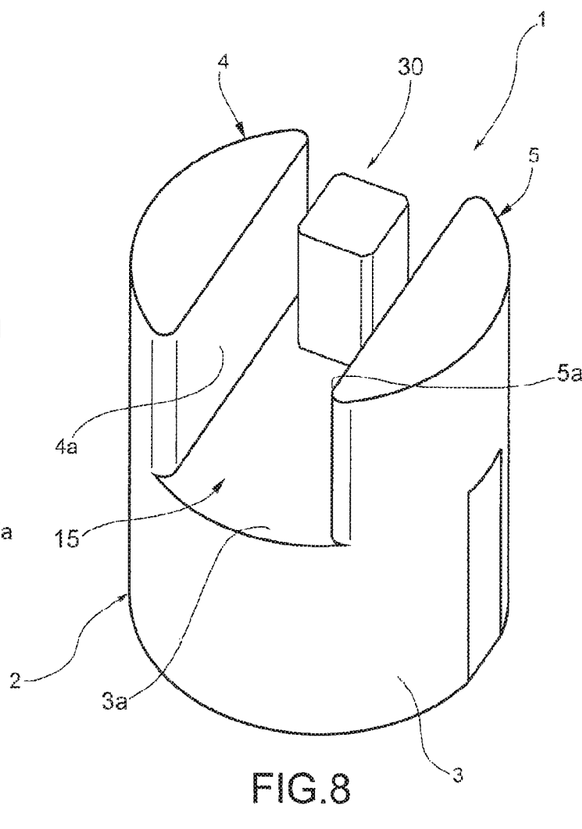
FIG. 8 is a perspective view of another variant embodiment.
Figure 9:
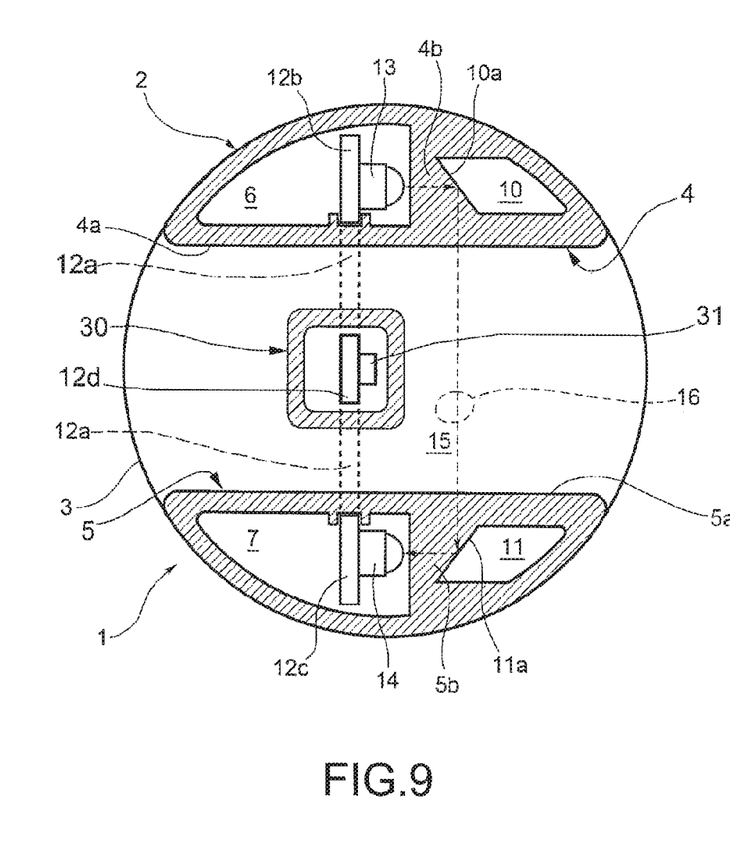
FIG. 9 is a sectional view of the device according to FIG. 8.

FIGS. 8 and 9 of the attached drawings show a further variant embodiment. In these figures, parts and elements described previously have again been given the same reference numerals as those used previously.

The variant according to FIGS. 8 and 9 is somewhat similar to the embodiment according to FIGS. 3 and 4, or to the embodiment according to FIG. 5.

With reference to FIG. 8, in said variant the housing 2 forms a further appendage 30 which extends from the portion 3a into the passage 15 between the appendages 4 and 5, preferably in a direction parallel to these appendages.

The appendage 30 is hollow (see FIG. 9), and a further portion 12d of the circuit board 12, coplanar with the other portions 12a-12c of this circuit board, extends inside this appendage. The portion 12d bears an electrical temperature sensor 31, of a known type, intended to supply, in use, electrical signals indicative of the temperature of the washing bath in contact with the appendage 30.

The solution according to FIG. 9, in which the radiation travels along a portion 16 of optical path offset relative to the circuit board 12, advantageously enables the transmitter 13, the receiver 14 and the temperature sensor 31 to be mounted on a single circuit board.

In a further variant, not shown in the drawings, the housing 2 of the device has a configuration similar to that of FIGS. 6 and 7, and the temperature sensor is placed inside it, near the wall indicated by 20a in said figures, on the same circuit board 12 as that which bears the transmitter 13 and the receiver 14.

In all the variants described above, the optical path of the radiation beam between the transmitter and the receiver extends in a plane at an angle to the longitudinal directions of the appendages 4 and 5 of the housing 2, and in particular this plane is orthogonal to said longitudinal directions.

Clearly, provided that the principle of the invention is retained, the forms of application and the details of embodiment can be varied widely from what has been described and illustrated purely by way of non-limiting example, without thereby departing from the scope of protection of the invention as defined by the attached claims.

The invention claimed is:

1. A sensor device for optically detecting characteristics of a fluid, comprising
    a housing including a base portion and first and second appendages extending from the housing along respective longitudinal directions and at least partially facing one another, wherein in use said fluid is present between said first and second appendages,
    first and second optoelectronic devices capable of transmitting and receiving radiation, respectively, mounted in a housing cavity formed in the housing, in the first and second appendages of the housing respectively, said housing cavity being open towards the base portion of the housing;
    wherein in use a radiation beam transmitted by the first optoelectronic device propagates in an optical path which includes a portion crossing the fluid between said appendages and reaches the second optoelectronic device;
    wherein said optical path comprises a plurality of reflecting surfaces adapted to deflect the radiation beam between the optoelectronic devices and said fluid crossing portion,
    said reflecting surfaces being made integrally with said appendages of the housing;
    wherein first and second internal cavities are formed in distal portions of the first and second appendages of the housing, respectively, said first and second internal cavities being open towards the base portion of the housing;
    wherein said plurality of reflecting surfaces comprise first and second reflecting surfaces which border with the first and second internal cavities of said appendages; and
    wherein the first reflecting surface is interposed between the first optoelectronic device and the first internal cavity, and the second reflecting surface is interposed between the second internal cavity and the second optoelectronics device, wherein said optical path extends in a plane at an angle to the longitudinal directions of said appendages.

2. The device according to claim 1, wherein said at least one reflecting surface flat.

3. The device according to claim 1, wherein said at least one reflecting surface is shaped so as to impart a predetermined shape to the reflected beam.

4. The device according to claim 1, wherein
the first reflecting surface is adapted to deflect the radiation beam transmitted by the first optoelectronic device towards the aforesaid fluid crossing portion; and
the second surface is adapted to deflect the beam from said crossing portion towards the second optoelectronic device.

5. The device according to claim 4, wherein the first and second optoelectronic devices are carried by two portions of the same circuit board, which each extend in one of said appendages of the housing, said first and second optoelectronic devices being orientated so that the beam transmitted by the first and the beam received by the second are essentially parallel to one another.

6. The device according to claim 4, wherein the first and second reflecting surfaces are both flat.

7. The device according to claim 4, wherein the first reflecting surface is shaped so as to impart a predetermined shape to the reflected beam.

8. The device according to claim 4, wherein there are formed in the housing, at said first and second appendages,
a third reflecting surface arranged so as to reflect towards the first reflecting surface the beam transmitted by the first optoelectronic device; and
a fourth reflecting surface arranged so as to reflect towards the second optoelectronic device the beam reflected by the second reflecting surface.

9. The device according to claim 8, wherein the first optoelectronic device and the second optoelectronic device are mounted and orientated on essentially opposite sides, towards the third and fourth reflecting surface respectively.

10. The device according to claim 1, wherein said optical path extends in a plane orthogonal to the longitudinal directions of said appendages.

11. The device according to claim 1, wherein between said appendages there is formed a region made as a recess of the housing extending between the side wall and an end wall of said housing.

12. The device according to claim 1, further including a temperature sensor mounted in said housing.

13. The device according to claim 12, wherein the temperature sensor is mounted on the same circuit board as that bearing said optoelectronic devices.

14. The device according to claim 1, wherein the housing is a unitary structure including said first and second appendages and said first and second reflecting surfaces.

* * * * *